(12) United States Patent
Gut

(10) Patent No.: US 10,151,628 B2
(45) Date of Patent: Dec. 11, 2018

(54) METHOD FOR CHECKING THE FUNCTIONALITY OF A MOTOR VEHICLE, AND MOTOR VEHICLE

(71) Applicant: AUDI AG, Ingolstadt (DE)

(72) Inventor: Carsten Gut, Ingolstadt (DE)

(73) Assignee: AUDI AG, Ingolstadt (DE)

( * ) Notice: Subject to any disclaimer, the term of this patent is extended or adjusted under 35 U.S.C. 154(b) by 0 days.

(21) Appl. No.: 15/521,555

(22) PCT Filed: Sep. 25, 2015

(86) PCT No.: PCT/EP2015/001904
§ 371 (c)(1),
(2) Date: Apr. 24, 2017

(87) PCT Pub. No.: WO2016/062366
PCT Pub. Date: Apr. 28, 2016

(65) Prior Publication Data
US 2018/0066985 A1  Mar. 8, 2018

(30) Foreign Application Priority Data
Oct. 24, 2014  (DE) .................. 10 2014 015 796

(51) Int. Cl.
*G01J 1/42*  (2006.01)
*G01M 11/06*  (2006.01)
*B60C 11/00*  (2006.01)
*G01J 1/16*  (2006.01)
(Continued)

(52) U.S. Cl.
CPC ........... *G01J 1/4257* (2013.01); *B60C 11/005* (2013.01); *F21S 41/16* (2018.01); *G01J 1/16* (2013.01);
(Continued)

(58) Field of Classification Search
CPC ......... B60Q 11/005; G01J 1/16; G01J 1/4257; G01N 21/93; G01M 11/06; G01M 11/065
(Continued)

(56) References Cited

U.S. PATENT DOCUMENTS

2003/0183784 A1   10/2003 Kongable
2011/0249460 A1   10/2011 Kushimoto
(Continued)

FOREIGN PATENT DOCUMENTS

DE   10 2007 049 619 A1   4/2009
DE      102010048689 A1 *  5/2011  .......... G01M 11/068
(Continued)

*Primary Examiner* — Tri T Ton
(74) *Attorney, Agent, or Firm* — Seed IP Law Group LLP

(57) ABSTRACT

The invention relates to a method for testing the operability of a motor vehicle (10) with a headlamp (12) which comprises a laser (14) for generating by means of which a converter (16) for emitting converted light is excited, which is emitted by the headlamp (12) for generating a predeterminable light distribution (18) on a surface area (20) in a surrounding area of the motor vehicle (10), wherein the predeterminable light distribution (18) is set by a control device (22) of the headlamp (12). The object of the invention is to check the condition of the converter (16). A test pattern (26, 30) is set by the control device (22) as light distribution (18). The test pattern (26, 30) is detected on the surface area (20) by means of an optical detection device (24) of the motor vehicle (10). The detected test pattern (26, 30) is compared with at a predetermined reference pattern by an evaluation device (28) of the motor vehicle (10). The invention also relates to a motor vehicle (10), which is designed to carry out such a method.

20 Claims, 1 Drawing Sheet

(51) Int. Cl.
*G01N 21/93* (2006.01)
*F21S 41/16* (2018.01)

(52) U.S. Cl.
CPC .......... *G01M 11/06* (2013.01); *G01M 11/065* (2013.01); *G01N 21/93* (2013.01)

(58) Field of Classification Search
USPC ................................................ 356/121–127
See application file for complete search history.

(56) References Cited

U.S. PATENT DOCUMENTS

| | | | |
|---|---|---|---|
| 2013/0257274 A1* | 10/2013 | Sekiguchi | ............. B60Q 1/143 315/82 |
| 2013/0265561 A1* | 10/2013 | Takahira | ................... F21V 7/06 356/3 |
| 2014/0003070 A1* | 1/2014 | Nakaya | .................... B60Q 1/08 362/466 |
| 2014/0254188 A1 | 9/2014 | Masuda et al. | |
| 2015/0092047 A1* | 4/2015 | Ryu | ......................... B60R 1/00 348/135 |

FOREIGN PATENT DOCUMENTS

| | | | | |
|---|---|---|---|---|
| DE | 10 2010 028 949 A1 | 11/2011 | | |
| DE | 10 2012 023 126 A1 | 5/2014 | | |
| DE | 10 2013 201 382 A1 | 7/2014 | | |
| JP | 2011-157022 A | 8/2011 | | |
| KR | 101307103 B1 * | 9/2013 | ............ | G01N 21/93 |

* cited by examiner

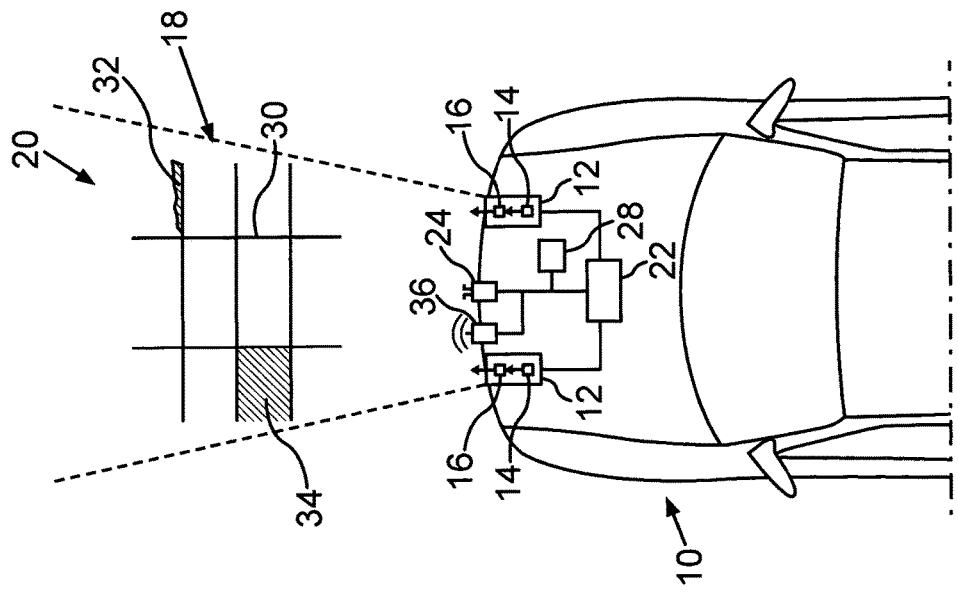
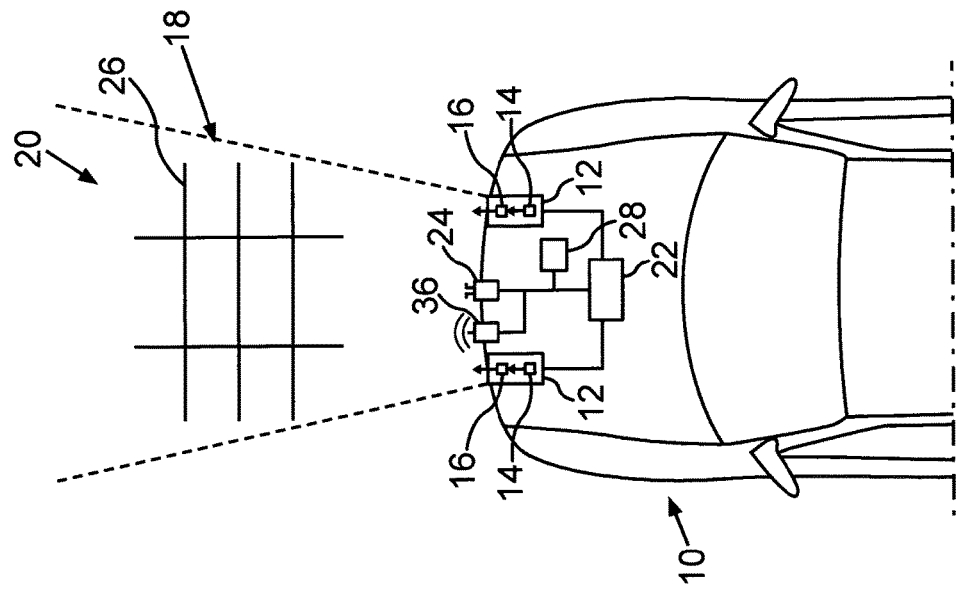

METHOD FOR CHECKING THE FUNCTIONALITY OF A MOTOR VEHICLE, AND MOTOR VEHICLE

TECHNICAL FIELD

The invention relates to a method for testing the operability of a motor vehicle according to the preamble of claim 1. In addition, the invention relates to a motor vehicle.

BACKGROUND INFORMATION

In the case of headlamps for motor vehicles, a laser can be used as a light source. By means of this laser, a converter for emitting converted light can be excited. Such a converter may, for example, comprise a crystal element of Ce: YAG, a particular form of yttrium aluminum garnet. The laser is usually used to generate light with a particularly high light intensity in a particularly narrow wavelength range. If excited, the converter emits light in another, particularly broad wavelength range, i.e., it converts the light generated by the laser. Thus, in particular, white light can be generated with, for example, a temperature of 5,500 Kelvin, which is perceived as particularly pleasant by all road users.

The light dissipated by the converter is emitted by the headlamp for generating a predeterminable light distribution on a surface area in a surrounding area of the motor vehicle. Thus, the predeterminable light distribution can be set by a control device of the headlamp, for example, by means of a pivotable micro-mirror or a mirror array, which is also referred to as a digital micromirror device. The motor vehicle can also comprise an optical detection device, by means of which, for example, other road users can be detected. The light distribution can then be set, for example, as a function of these other detected road users, so that these are preferably not blinded by the light distribution.

In general, the converter of a headlamp of a motor vehicle with a laser as a light source can be damaged by mechanical forces and aging processes, so that the operability of the headlamp and thus also of the motor vehicle is impaired. Damage can lead to eye irritation and glare in other road users.

A directional system with laser and converter for an infrared sensor is known from US 2003/0183784 A1. In the case of correct alignment, the converter is excited to emit light in a certain pattern, so that it is recognizable that the infrared sensor is correctly aligned.

BRIEF SUMMARY

It is an object of the present invention to provide a method for testing the operability of a motor vehicle. Furthermore, it is an object of the invention to provide a motor vehicle by means of which such a method can be carried out.

This object is solved according to the invention by a method and a motor vehicle with the features of the independent claims. Advantageous embodiments with suitable further designs of the invention are provided in the remaining claims.

For this purpose, the motor vehicle comprises a headlamp which emits the light emitted by the converter for generating a predeterminable light distribution on a surface area in a surrounding area of the motor vehicle. The predeterminable light distribution can be adjusted by a control device of the headlamp, for example, by means of a pivotable micromirror or a mirror array, which is also referred to as a digital micromirror device (DMD). The motor vehicle can also comprise an optical detection device, by means of which, for example, other road users can be detected. The light distribution can then be set, for example, as a function of these other detected road users, so that these are preferably not blinded by the light distribution.

The method according to the invention for testing the operability of a motor vehicle is characterized by the following steps:
- a test pattern is set by the control device as light distribution;
- the test pattern is detected on the surface area by means of an optical detection device;
- the detected test pattern is compared with at least one predetermined reference pattern by an evaluation device of the motor vehicle.

Thus, the actual light distribution of the headlamp can be compared with an expected light distribution so as to be able to detect damage to the converter.

In the simplest case, the test pattern may comprise the turning on and off of the light distribution, more complex test patterns may each have a certain light-dark boundary, different colors and color traces, different brightnesses, different positions on the surface, shapes of areas of specific brightness. The reference pattern can simulate a test pattern of a light distribution generated by an undamaged headlamp. Alternatively, the reference pattern can also simulate a light distribution of a headlamp with a damaged converter, so that specific sources of error or defects can also be directly identified by a comparison. In the case of a headlamp with several converters, a damage can also be assigned to the respective converter.

The optical detection device is usually already installed in motor vehicles with a headlamp with adjustable light distribution so that no additional detection device is necessary. Thus, the method enables the operability of a motor vehicle to be checked particularly simply and cost-effectively, in particular by the motor vehicle itself and without other external devices.

Damages and/or malfunctions of the converter can also be distinguished from damage and/or malfunctions of other components of the headlamp by additional sensors installed in the headlamp or the motor vehicle. For example, a malfunction of the laser can be detected by a luminosity monitoring by means of a photodiode, the control device can be monitored by a voltage monitoring, and/or a possible overheating of the headlamp can be detected by means of a temperature sensor.

In a further advantageous embodiment of the invention, the test pattern is compared with the reference pattern by means of the evaluation device by means of at least one of the following properties: a light-dark boundary, a position, a brightness, a shape and a color. Local or spectral shifts, geometric distortions and color gradients of the light distribution can thus also be tested. The area of the converter, which is damaged, can in particular be identified by the light-dark boundary. On the basis of the position of the light distribution, an undesirable local displacement of the converter in the headlamp can be detected, which is also regarded as damage. On the basis of the brightness, an aging can be detected, in particular in the form of a darkening of the converter, and in particular mechanical errors such as broken-off edges of the converter can be located based on the shape. On the basis of the color, aging processes with a discoloration of the converter and/or a change in an expected conversion of the light can be detected particularly well. Cracks in the crystal of a converter can also be detected.

It is particularly advantageous for the method if the reference pattern itself is generated by the motor vehicle, a further light distribution being set, detected and stored as the reference pattern. As a result, symmetry can be checked in particular. In addition, it is thus possible, for example, to compare a first headlamp with a second headlamp of the motor vehicle so as to test the operability in a particularly simple manner. In addition, at least one additional error-specific test pattern can subsequently be generated in order to be able to assign error sources to a specific area of the converter. In addition, an influence by the surrounding area with its surface area on the result of testing the operability of the motor vehicle can be reduced (bias compensation).

It is particularly advantageous if the test pattern is set for a predetermined duration which is below a duration from which the test pattern is visually perceptible for a human being. Such a duration is, for example, less than or equal to a $\frac{1}{20}$ second, in particular less than or equal to a $\frac{1}{30}$, $\frac{1}{40}$, $\frac{1}{50}$, $\frac{1}{60}$, $\frac{1}{70}$, $\frac{1}{80}$, $\frac{1}{90}$ or a $\frac{1}{100}$ second. This makes it possible to carry out the operability of the motor vehicle while driving without a disturbance of the driver and/or other road users. Thus, a so-called online testing of the operability of the motor vehicle while driving can take place. This makes regular testing possible, for example, with a repetition frequency in a range from 1 minute to 300 minutes, so that errors of the converter can be detected particularly promptly.

It is further advantageous if the test pattern is set for a duration which is dependent on a comparison result of a previous comparison of a detected test pattern with a reference pattern. Thus, for example, the duration for which the test pattern is set can be made dependent on a prior test of the operability of the motor vehicle. This makes it possible to carry out a new test with a larger and/or different test pattern when a defect has been detected in a previous test. The larger and/or other test patterns can be, for example, one of the more complex test patterns already described above. This makes possible a particularly simple and accurate validation of a test result. By means of the test pattern appearing with this longer duration, even small defects and sources of error can be identified and/or assigned exactly to an area of the converter.

In a further particularly advantageous embodiment of the method, it is provided that a condition, in particular a geometry and/or reflection property of the surface area illuminated by the light distribution, is detected by means of the detection device and/or an additional sensor device and the test pattern as a function of this recognized condition is compared with the reference pattern. As a result, a corruption of the test result can be prevented thanks to the condition of the surface area. For example, unevenness in a road or distortions through scrub can be filtered out. For the invention, image recognition algorithms are available from the prior art. Alternatively, it is thus also possible to adjust the light distribution of the test pattern as a function of the condition of the surface area illuminated by the light distribution in such a way that this condition is also taken into account and has no or very little influence on the projected test pattern. Alternatively or additionally, it can also be provided that the test pattern is set only when the surface is, for example, level enough and thus the probability of an incorrect test result is particularly low.

An additional sensor device may be, for example, a radar or an ultrasonic sensor present in the motor vehicle. A coupling, for example with GPS coordinates, is also possible in order to carry out a test always approximately at the same location. Thus, it can be assumed, for example, that the illuminated surface is always in approximately the same condition. This could be, for example, the road in front of the home of the owner of the motor vehicle. A coupling with a route planning of a navigation device is also possible. This means that a test can always be carried out before the start of a trip and/or on arrival. Alternatively, it is otherwise also possible to carry out the method in front of a test wall in order to avoid influences on the test result due to the condition of the illuminated surface area.

In a particularly advantageous embodiment of the invention, it is provided that the headlamp is calibrated as a function of a result of the comparison of the test pattern with the reference pattern. This calibration can be an alignment of the headlamp to an axle of the motor vehicle. However, it is particularly advantageous if the light distribution is adjusted by the control device after the operability test has been performed so that the test pattern and the reference pattern deviate only very slightly from one another in order to calibrate the headlamp. This can at least partially compensate for damages to the headlamp and, in particular, the converter, until repair or replacement of the headlamp is possible. In this way, in particular eye irritations and glare of other road users by a damaged headlamp can be avoided particularly well.

It is further advantageous if an error message is output by the evaluation device when the test pattern deviates from the reference pattern by a predetermined threshold value during the comparison. Thus, in particular, a specific feature of the test pattern and of the reference pattern such as the light-dark boundary, the position, the brightness, the shape and the color of the light distribution can be compared with a threshold value. The error message can be output to the driver of the motor vehicle by means of an optical or acoustic signal, alternatively or additionally, it can be stored in a memory of the motor vehicle in order to be able to read it out again for subsequent maintenance purposes. The error message may contain further information about the suspected damage and/or a detected malfunction. Of course, it is also possible, for example, to transmit the error message wirelessly to a workshop or maintenance facility.

The advantages and embodiments described above in connection with the method according to the invention apply in such manner to the motor vehicle which is designed to carry out such a method.

In a further advantageous embodiment of the motor vehicle, it is provided that the optical detection device comprises a camera and/or an infrared camera. A camera or infrared camera is particularly cost-effective and usually already installed in motor vehicles with adjustable light distribution. In particular, such optical detection devices can also be used by other motor vehicle systems, for example driver assistance systems. A camera makes it particularly possible to detect the test pattern in a wavelength range, as is also detected by the human eye. An infrared camera has the advantage that parts of the light spectrum or wavelength regions which are not detected by the human eye can also be detected. It is thus possible to detect aging processes in the converter particularly early.

BRIEF DESCRIPTION OF THE DRAWINGS

Additional advantages, features and details of the invention will become apparent from the following description of the preferred embodiments as well as from the drawings; these are shown in:

FIG. 1 a schematic top view of a motor vehicle with a headlamp which generates a first light distribution; and FIG. 2 an additional top view of the motor vehicle as in FIG. 1, wherein the headlamp generates a second light distribution.

DETAILED DESCRIPTION

The embodiment described in the following is a preferred embodiment of the invention. In the embodiment, however, the described components of the embodiment represent individual features of the invention which are independent of one another and which also form the invention independently of each other and thus also individually or in a combination other than the one shown are considered part of the invention. Furthermore, the described embodiment can also be supplemented by additional of the already described features of the invention.

FIG. 1 and FIG. 2 show a motor vehicle 10 with two headlamps 12 in a schematic top view. In this case, the headlamps 12 comprise a laser 14 for generating light, by means of which a converter 16 for emitting converted light is excited. This light dissipated by the converter 16 is emitted by the headlamp 12 for generating a predeterminable light distribution 18 on a surface area 20 in a surrounding area of the motor vehicle 10. The surface area 20 is, for example, a road, but it can also be a test wall in front of the motor vehicle 10.

The predeterminable light distribution 18 is set by a control device 22 of the headlamp 12. In the case shown, the two headlamps 12 are connected to a common control device 22 which, for example, controls an adjustable micromirror in each headlamp 12. By means of the micromirror, the light is emitted from the headlamp 12 in such a way that the light distribution 18 is built up, for example, line-wise on the surface area 20. The control device 22 can also set the light distribution 18 as a function of additional road users detected by the optical detection device 24.

The method for testing the operability of a motor vehicle 10 with the headlamps 12 is characterized by the following steps:

A test pattern 26 is set by the control device 22 as the light distribution 18. In the example shown in FIG. 1, five line-shaped areas of the light distribution 18 on the surface area 20, i.e. on the road, are, for example, not illuminated or illuminated to a lesser extent.

The test pattern 26 is detected on the surface area 20 by means of the optical detection device 24 of the motor vehicle 10.

The detected test pattern 26 is compared with at least one predetermined reference pattern by an evaluation device 28 of the motor vehicle 10.

If, for example, the converter 16 is damaged by mechanical forces and/or aging processes, the generated test pattern 26 will deviate from the reference pattern when compared to it. Then, an error message can be output by the evaluation device 28 accordingly. For example, FIG. 1 shows the test pattern 26 emitted from an undamaged headlamp 12 while the test pattern 30 of the light distribution 18 in FIG. 2 is generated by a damaged converter 16.

From a motor vehicle 10, at the right rear viewed in the direction of travel, a subarea 32 of the light distribution 18 of FIG. 2 in comparison with FIG. 1 has a pronouncedly deformed broader, non-illuminated subarea 32 instead of a linear area. This allows, for example, to assume a broken converter 16 or a converter 16 with cracks. An additional subarea 34, viewed from the motor vehicle 10 in the direction of travel on the left side of the light distribution 18, likewise exhibits a change. Here the light distribution 18 is, for example, illuminated less brightly or has a different color. This makes it possible, for example, to assume an aging of the converter 16, wherein said converter, for example, has discolored and/or is no longer able to be excited as well for emitting light by the laser 14. The respective subarea 32, 34 of the test pattern 26, 30 or of the light distribution 18 can in this case be assigned directly to a subregion of the converter 16. The physical position of the damage, i.e. the crack and/or the discoloration of the converter 16, can thus also be determined.

The reference pattern can be fixedly stored in the evaluation device 28. It may either correspond to a test pattern 26 generated by an undamaged converter 16, or to a test pattern 30 generated by a damaged converter 16. A plurality of different reference patterns can also be provided, which are compared with the test pattern 26, 30.

The reference pattern itself can be generated by the motor vehicle 10, by setting, detecting, and storing an additional light distribution 18. As a result, influences by surrounding areas on the result of the testing of the operability of the motor vehicle 10 can be particularly well reduced. In addition, it is thus possible, for example, to compare the two headlamps 12 of the motor vehicle 10 with one another. For example, a reference pattern can be generated in a particularly simple manner, for example by first generating a pattern by the left headlamp 12 of the motor vehicle 10 and then by the right headlamp 12 of the motor vehicle 10. Subsequently, only a comparison of these two patterns is necessary. In this case, the fact that symmetrical light distributions can be generated by the two headlamps 12 is used.

Thus, each test pattern 26, 30 can also be used simultaneously as a reference pattern for an additional test of the operability of the motor vehicle 10. Thus, FIG. 1 can also be understood in such a way that a reference pattern is shown here in the light distribution 18. FIG. 2 then shows the test pattern 30, which is compared with the reference pattern formed as test pattern 26, as shown in FIG. 1. Due to a damage of the converter 16, the test pattern 30 thereby deviates from the reference pattern, i.e. the test pattern 26. The reference pattern formed as a test pattern 26 can in this case be set, detected and stored by the motor vehicle 10 itself. However, it can also be stored in a memory of the motor vehicle 10 during manufacture of the motor vehicle 10.

During the test, the test pattern 26 and/or 30 is preferably set for a predetermined duration and illuminates the surface area 20 which is below a duration at which the test pattern 26 and/or 30 is visually perceptible by a human being. Thus, the headlamp 12 of the motor vehicle 10 can be checked periodically during a journey of the motor vehicle 10 without this being obvious to or disturbing the driver or another road user. As a result, the functionality of the motor vehicle 10 and its headlamps 12 can be monitored during the entire use.

If, during the test, a subarea deviating from the reference pattern, such as, for example, the subarea 32 or 34, is detected by the optical detection device 24, the test pattern 26 and/or 30 can be set for a duration which depends on the result of this prior test. For example, in the case of a detected malfunction, a particularly complex test pattern is emitted onto the surface area 20 for a particularly long duration. Thus the prior test can be made plausible particularly well. Likewise, it is thus possible to particularly closely test the deviation in the comparison, and in particular to determine a location of a damage to the converter 16. In this case, it is not even disadvantageous if this particularly complex test pattern is then perceptible to the driver of the motor vehicle 10, since this can simultaneously be used to issue an error message.

It is particularly useful if a condition of the surface area 20 is detected by means of the detection device 24 and/or an additional sensor device 36 and the test pattern 26, 30 is compared with the reference pattern as a function of this condition. As a result, external influences on the result of the test, such as a reflection of the light distribution 18 by, for example, a wet roadway and/or a distortion of the test pattern 26, 30 by, for example, an uneven roadway or objects on the road, can be prevented. As a result, the method for testing the operability of the motor vehicle 10 is particularly robust.

If the optical detection device 24 comprises a camera, the spectrum of the wavelength of the light, which is also detected by the human eye, can be detected in particular. With an optical detection device 24 comprising an infrared camera, other spectral ranges or wavelength ranges of the light can be detected in order to detect in particular aging phenomena at an early stage. The additional sensor device 36 may comprise, for example, a radar or an ultrasonic sensor. By means of such an additional sensor device 36, the condition of the surface area 20, in particular its geometry, can be detected particularly well. Such an additional sensor device 36 is already frequently installed, in particular, in motor vehicles with driver assistance systems. Correspondingly, the additional sensor device 36 can be used for the method with little or no additional costs.

In addition, the comparison of the test pattern 26, 30 with the reference pattern can be used for a calibration of the headlamp 12. In particular, the light distribution 18 can be set by the control device 22 in such a way that the test pattern 26, 30 differs very little from the reference pattern. As a result, damage to the converter 16 can be compensated at least in part. In particular, it is, for example, possible to no longer excite with the laser 14 the damaged subarea of the converter 16, which has been localized by the method for testing the operability and/or no longer emit the light dissipated by this area from the headlamp 12 for generating the light distribution 18.

Furthermore, it is possible to provide threshold values for certain features of the light distribution 18, from which an error message is output by the evaluation device 28. If the deviation is below this threshold value, the result of the test is, for example, below a confidence level, and it is not possible to determine with certainty whether a malfunction is present or not.

By means of the method according to the invention, the condition of the luminescent, in particular fluorescent converter 16 can be analyzed very precisely by the generation of a test pattern 26, 30 in the form of a test image. The test pattern 26, 30 on the road resulting from generating the test image is dependent on the condition of the converter 16. If this is damaged, the test pattern 26, 30 will deviate from a reference pattern. If the deviation exceeds a defined threshold value, the headlamp 12 and/or the laser 14 can be turned off and an error message can be output. In this case, a detection device 24 already provided for the motor vehicle 10 can be used. In addition to the monitoring, the headlamp 12 can also be calibrated by the test patterns 26, 30. For the implementation, an optical detection device 24 with a resolution corresponding to the line-by-line assembled light distribution 18 is to be selected. In this way, all the errors in the test pattern 26, 30 can be detected and these can also be assigned particularly well to a subarea of the converter 16.

The test pattern 26, 30 should be assembled so quickly during a driving operation of the motor vehicle 10 that this is not recognized by the human eye. Alternatively or additionally, it is also possible to carry out a very detailed test at a start of the motor vehicle 10. This detailed test can also be carried out if a potential error has already been detected during a previous test.

If an optical detection device 24 is used which cannot only detect gray scale values but also analyzes the color of the light distribution 18, potential sources of error can be analyzed particularly precisely. The color of the light emitted by the headlamp 12 in particular may be changed if the converter 16 is damaged. Where appropriate, the test may be carried out only under certain conditions, such as on highways without oncoming traffic.

Overall, the example shows how an error recognition of dynamic headlamp systems is created by the invention.

The invention claimed is:

1. A method, comprising:
testing a headlamp of a motor vehicle, the headlamp including a laser and a converter excitable by the laser, the headlamp configured to generate light in a light distribution on a surface area in a surrounding area of the motor vehicle, wherein the light distribution is controlled by a control device, the testing including:
setting a test pattern with the control device;
generating the light distribution on the surface area in the surrounding area of the motor vehicle in accordance with the test pattern by the headlamp;
detecting the test pattern on the surface area using an optical detection device of the motor vehicle;
comparing the detected test pattern with at least one predetermined reference pattern by an evaluation device of the motor vehicle, the reference pattern corresponding to the test pattern generated from an undamaged or damaged headlamp; and
detecting an aging or a crack of the converter by comparing at least one of a brightness and a color in the detected test pattern and the reference pattern by the evaluation device.

2. The method according to claim 1, wherein the evaluation device compares at least one of a light-dark boundary, a position, and a shape in the detected test pattern and the reference pattern.

3. The method according to claim 1, further comprising generating the reference pattern by the motor vehicle, by setting and detecting an additional light distribution and storing it as the reference pattern.

4. The method according to claim 1, wherein the test pattern is set for a predetermined duration, which is below a duration from which the test pattern is visually perceptible to a human being.

5. The method according to claim 1, wherein the test pattern is set for a duration which is dependent on a comparison result of a previous comparison of a detected test pattern with a reference pattern.

6. The method according to claim 1, wherein a condition of the surface area illuminated by the light distribution is recognized by the detection device or an additional sensor device, and the test pattern is compared with the reference pattern in dependence on this recognized condition.

7. The method according to claim 1, wherein the headlamp is calibrated with the reference pattern as a function of a result of the comparison of the test pattern.

8. The method according to claim 1, wherein
an error message is output by the evaluation device when the test pattern deviates from the reference pattern by a predetermined threshold value during the comparison.

9. A motor vehicle, comprising:
a headlamp including:
    a laser that generates light in operation; and
    a converter coupled to the laser, wherein the converter emits converted light in operation that generates a light distribution onto a surface area in a surrounding area of the motor vehicle;
an optical detection device that in operation detects the light distribution on the surface area;
a control device coupled to the headlamp, wherein the control device in operation controls the light distribution of the headlamp; and
an evaluation device that in operation detects an aging or a crack of the converter by analyzing at least one of a brightness and a color in the detected light distribution.

10. The motor vehicle according to claim 9, wherein the optical detection device comprises a camera or an infrared camera.

11. The motor vehicle of claim 9, wherein the control device in operation:
    selects a test pattern; and
    outputs the test pattern from the headlamp on the surface area.

12. The motor vehicle of claim 11, wherein the optical detection device detects in operation the test pattern on the surface area.

13. The motor vehicle of claim 12, further comprising an evaluation device that compares the test pattern detected by the optical detection device and compares, in operation the detected test pattern with a reference pattern.

14. The motor vehicle of claim 13, wherein the evaluation device compares brightness and color of the reference pattern and the test pattern.

15. The method of claim 1, further comprising determining as a function of a position of a modified subarea of the light distribution a position of damage to the converter.

16. The method of claim 1, further comprising setting the test pattern for a predetermined duration that is less than or equal to $\frac{1}{20}$ a second.

17. The method of claim 6, wherein the condition of the surface area illuminated by the light distribution is a geometry or reflection characteristic of the surface area.

18. A device, comprising:
a headlamp including a laser and a converter excitable by the laser;
a control device coupled to the headlamp, wherein the control device in operation:
    selects a test pattern; and
    emits the test pattern through the headlamp to a surface;
an optical detection device coupled to the control device, wherein the optical detection device in operation:
    detects the test pattern from the surface; and
an evaluation device coupled to the optical detection device and the control device, wherein the evaluation device in operation:
    compares the test pattern with a reference pattern; and
    detects an aging or a crack of the converter by detecting differences in at least one of a brightness and a color between the test pattern and the reference pattern.

19. The device of claim 18 wherein the evaluation device in operation outputs a signal indicative of damage to the headlamp in response to the detected differences.

20. The device of claim 1 wherein the motor vehicle includes a second headlamp having a second laser and a second converter excitable by the second laser and the at least one predetermined reference pattern is generated by generating a second light distribution on a second surface area in the surrounding area of the motor vehicle in accordance with the test pattern by the second headlamp and detecting the test pattern on the second surface area using the optical detection device.

* * * * *